US005575929A

United States Patent [19]
Yu et al.

[11] Patent Number: 5,575,929
[45] Date of Patent: Nov. 19, 1996

[54] METHOD FOR MAKING CIRCULAR TUBULAR CHANNELS WITH TWO SILICON WAFERS

[75] Inventors: Conrad M. Yu, Antioch; Wing C. Hui, Campbell, both of Calif.

[73] Assignee: The Regents of the University of California, Oakland, Calif.

[21] Appl. No.: 464,020

[22] Filed: Jun. 5, 1995

[51] Int. Cl.⁶ .................................................. B01D 15/08
[52] U.S. Cl. ............................... 216/10; 216/33; 216/56; 216/99
[58] Field of Search ........................... 156/647.1; 216/8, 216/33, 56, 99, 10

[56] References Cited

U.S. PATENT DOCUMENTS

| | | | |
|---|---|---|---|
| 3,977,925 | 8/1976 | Schwabe | 156/13 |
| 4,115,793 | 9/1978 | Nishizawa | 357/22 |
| 4,326,771 | 4/1982 | Henry et al. | 156/644 |
| 5,223,086 | 6/1993 | Terada et al. | 156/651 |
| 5,255,376 | 7/1993 | Feaver et al. | 156/644 |

FOREIGN PATENT DOCUMENTS

| | | |
|---|---|---|
| 62-083661 | 4/1987 | Japan. |
| 62-108156 | 5/1987 | Japan. |
| 03263001 | 11/1991 | Japan. |
| 06084731 | 3/1994 | Japan. |

OTHER PUBLICATIONS

"Chemical Isotropic Etching of Single–Crystal Silicon For Acoustic Lens of Scanning Acoustic Microscope", Jpn. J. Appl. Phys. vol. 32 (May 1993), Pt. 1, No. 5B, Hashimoto et al.; pp. 2543–2546.

"Integrated Circuit Fabrication Technology"; Elliot; ©1992; McGraw–Hill; NY, NY.

*Primary Examiner*—R. Bruce Breneman
*Assistant Examiner*—George A. Goudreau
*Attorney, Agent, or Firm*—Henry P. Sartorio; Richard B. Main

[57] ABSTRACT

A two-wafer microcapillary structure is fabricated by depositing boron nitride (BN) or silicon nitride ($Si_3N_4$) on two separate silicon wafers (e.g., crystal-plane silicon with [100] or [110] crystal orientation). Photolithography is used with a photoresist to create exposed areas in the deposition for plasma etching. A slit entry through to the silicon is created along the path desired for the ultimate microcapillary. Acetone is used to remove the photoresist. An isotropic etch, e.g., such as $HF/HNO_3/CH_3COOH$, then erodes away the silicon through the trench opening in the deposition layer. A channel with a half-circular cross section is then formed in the silicon along the line of the trench in the deposition layer. Wet etching is then used to remove the deposition layer. The two silicon wafers are aligned and then bonded together face-to-face to complete the microcapillary.

7 Claims, 3 Drawing Sheets

METHOD FOR MAKING CIRCULAR TUBULAR CHANNELS WITH TWO SILICON WAFERS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to micro-instrumentation and more particularly to the fabrication of circular microcapillaries in silicon wafers, particularly for use in portable gas chromatographs.

2. Description of Related Art

Gas chromatographs generally comprise three basic parts, an injector, a column, and a detector. The method of the invention for etching microchannels in silicon wafers relates in particular to a highly miniaturized and portable gas chromatograph (GC) and provides a method to construct a column for such a device.

In a GC, gas samples are carried into a column by a carrier gas. The propagation front of the gas and how it diffuses into and back out of the column itself are highly dependent on the inside cross-sectional geometry of the column. A circular cross-section column is ideal and produces the best results, as the lighter molecules of sample gas will diffuse faster than the heavier molecules and a circular column presents a uniform path, regardless of the direction of outward diffusion into the column walls.

The prior art has not succeeded in the fabrication of circular cross-section microcapillaries in silicon for use in GC columns. Conventional attempts to fabricate columns have resulted in squared-bottom trenches in one wafer that are capped by another wafer, typically some second, different material that produces thermal coefficient-of-expansion problems.

Silicon wafers are flat and are universally processed from one side, e.g., with depositions, implants, masks and etching. Semiconductor fabrication processes are conventionally used to create non-electronic microstructures using silicon, oxides and metals.

Because of the way masks must be used with etchants, it is practically impossible to create a round tube or capillary in a single wafer of silicon. Two obstacles are encountered. First, the etching of half-round microchannels in silicon wafers has proven impossible with conventional methods. And second, joining together matching wafers in a sandwich with the completed round capillary in between has proven to be very tedious. The conventional art in matching the geometries of features on each of the two respective halves is very precise, but the joining together of two separate silicon wafers does not lend itself to such easy precision. Mis-registrations of even a few mils can cause ruinous overlaps of the two halves of ten to twenty percent and more.

SUMMARY OF THE INVENTION

An object of the present invention is to provide a method for fabricating semicircular cross section microchannels in the surface of silicon wafers.

A further object of the present invention is to provide a method for forming whole microcapillaries from two silicon wafers with mirror-image semicircular microcapillaries.

Briefly, a method of the present invention for fabricating semicircular microchannels in the surface of silicon wafers comprises depositing a protective layer of boron nitride (BN) or silicon nitride ($Si_3N_4$) on two separate silicon wafers (e.g., crystal-plane silicon with [100] or [110] crystal orientation). Photolithography is used with a photoresist to create exposed areas in the deposition for plasma etching. A narrow slit entry through to the underlying silicon is created along the path desired for a much-wider microcapillary. Acetone is used to remove the photoresist. An isotropic etch, e.g., such as $HF/HNO_3/CH_3COOH$, then is used to erode away the silicon through the trench opening in the protective layer. A channel with a half-circular cross section is then formed in the silicon along the line of the trench in the deposition layer. Wet etching is then used to remove the deposition layer. The two silicon wafers are aligned and then bonded together face-to-face to complete the microcapillary.

An advantage of the present invention is that a method is provided for making microchannels in silicon with semicircular cross sections.

Another advantage of the present invention is that a method is provided for fabricating a circular cross-section microcapillary from two silicon wafers joined together.

DETAILED DESCRIPTION OF THE INVENTION

Figure 1A:
FIG. 1 is a diagram of a method embodiment of the present invention for making a semicircular microchannel in a silicon wafer.
Figure 1B:
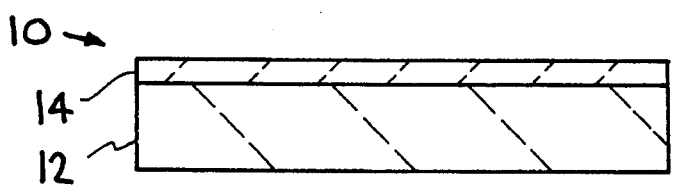
Figure 1C:
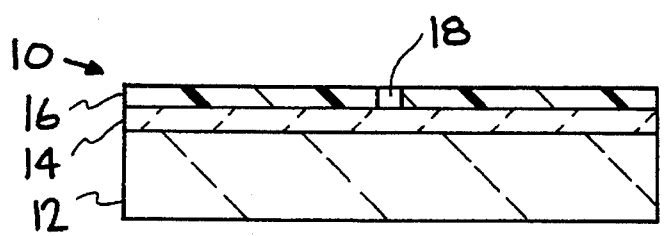
Figure 1D:
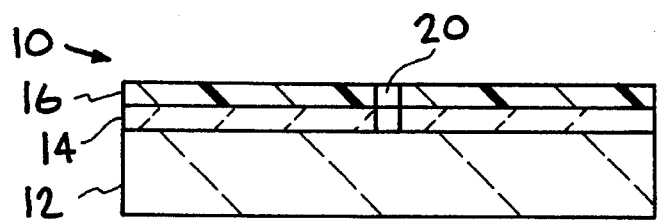
Figure 1E:
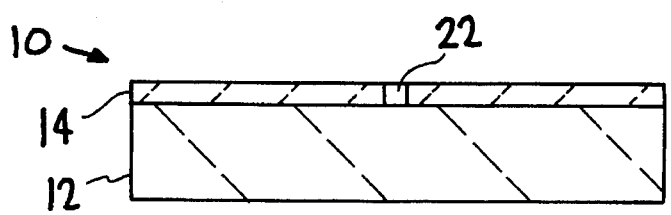
Figure 1F:
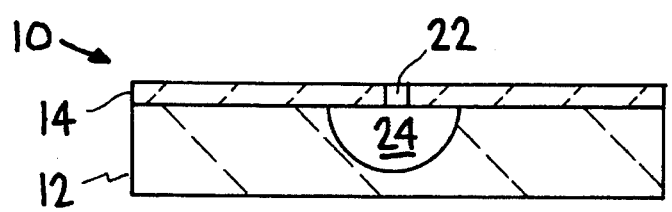
Figure 1G:
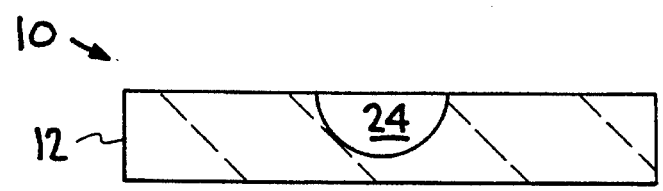

FIG. 1 shows a method of the present invention, referred to herein by the general reference numeral 10, for making a semicircular microchannel in a crystal-plane silicon wafer 12. A protective coating 14 is applied to the surface of the silicon wafer 12. The protective coating preferably comprises a material that is inert or at least resistant to attack from etchants. For example, boron nitride (BN) or silicon nitride ($Si_3N_4$) are used. A photoresist 16 is then applied and an opening 18 is made by photolithography. The opening 18 follows along a narrow line that defines the path the semicircular microchannel will follow. Plasma etching is used to open a hole 20 all the way through the photoresist 16 and protective coating 14 to expose the underlying silicon wafer 12. The width of the hole 20 is substantially less than the width intended for the microchannel. Acetone is used to wash away the photoresist, leaving a slit entry 22 from the hole 20 in coating 14. Isotropic etching through the slit entry 22 is used to erode the silicon material equally in all directions in the silicon from the slit entry 22 to form a semicircular cross-section microchannel 24. For example, $HF/HNO_3/CH_3COOH$ is used as an isotropic etchant. Wet etching removes the protective layer and exposes the microchannel 24.

In order to complete a whole microcapillary from two microchannels 24, two wafers 12 are processed as in the method 10, but the patterning with photolithography of the opening 18 in one silicon wafer 12 is made the mirror-image of the other opening 18 in the second silicon wafer 12. Then the two corresponding silicon wafers 12 with microchannels 24 are placed face-to-face and aligned and bonded together.

Copending United States Patent Application, serial number 08/465,068 (IL-9590), filed herewith, by Conrad M. Yu and Wing C. Hui, entitled, "MICROCAPILLARY AND METHOD FOR JOINING SILICON WAFERS IN THE FABRICATION OF MICROCAPILLARIES", describes methods for aligning the two wafers, and is incorporated herein by reference.

Figure 2A:
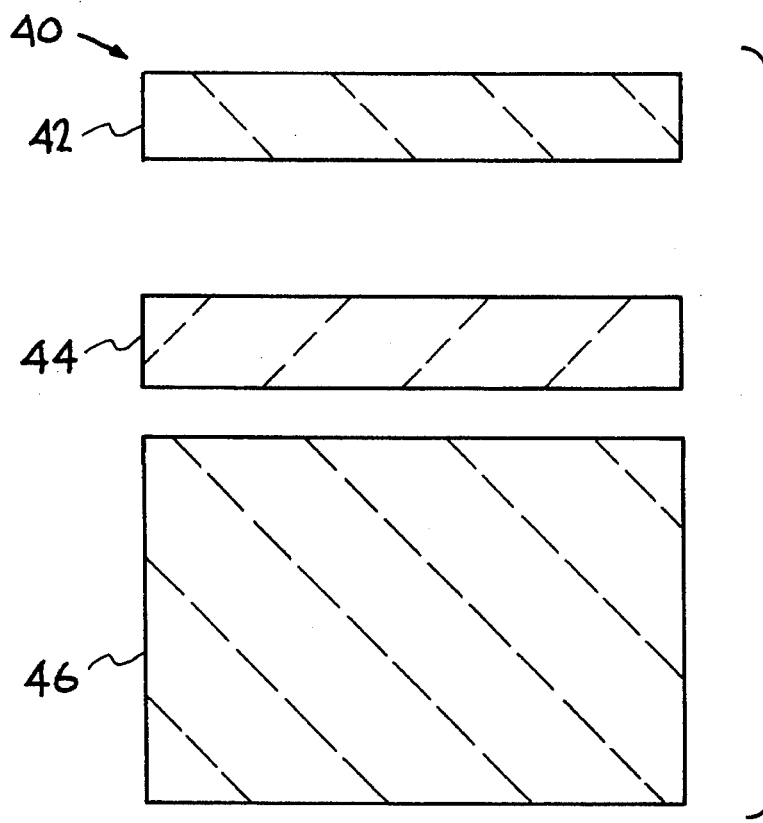
FIGS. 2A–2D are diagrams of a second method embodiment of the present invention for making a microcapillary from two silicon wafers using alignment holes and a post.
Figure 2B:
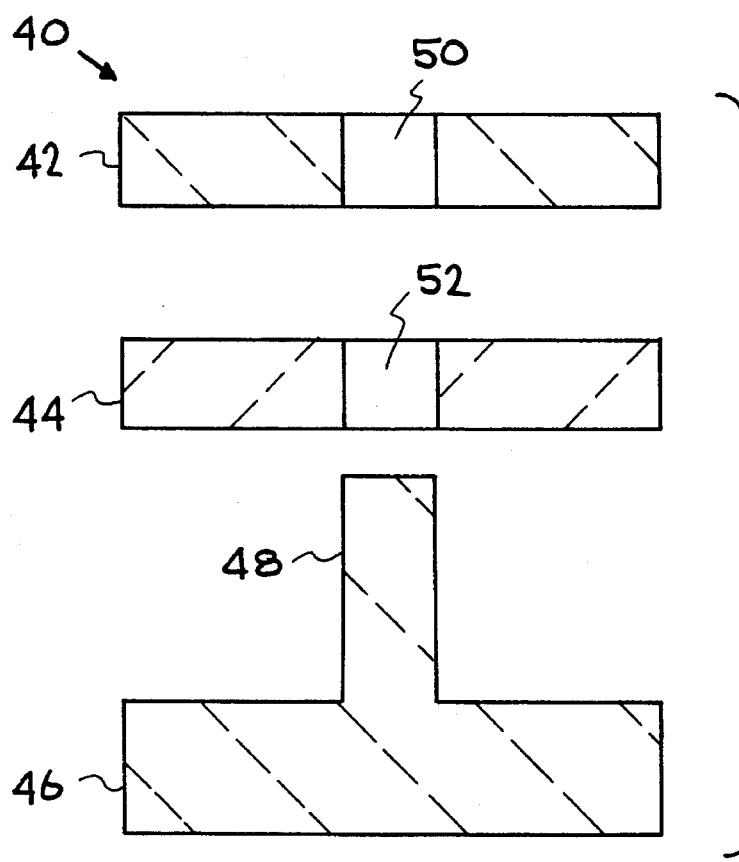
Figure 2C:
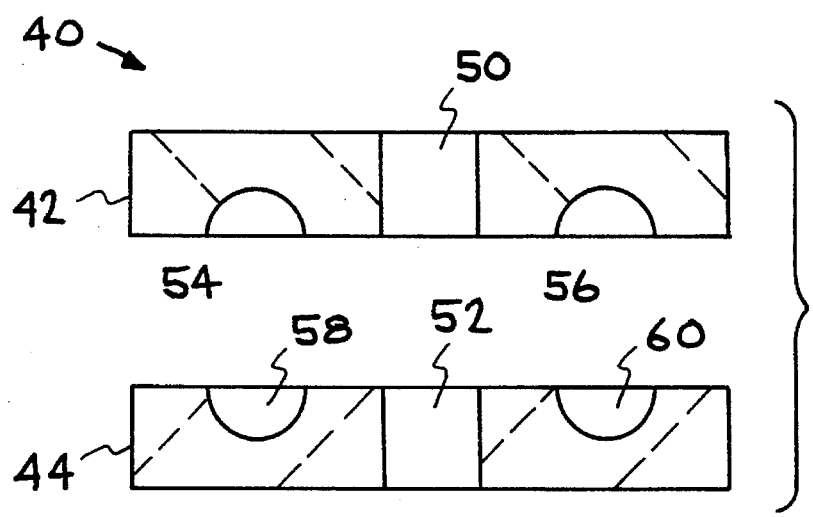
Figure 2D:
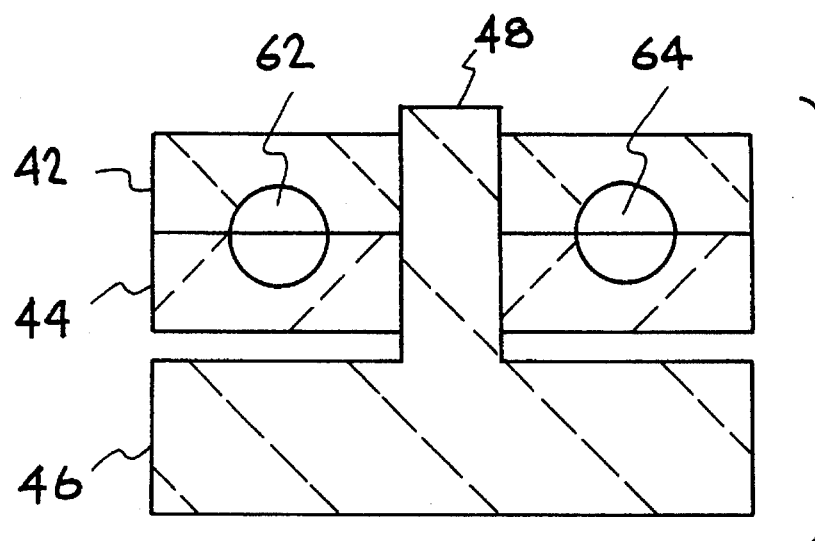

FIGS. 2A–2D show a method of the present invention, referred to herein by the general reference numeral 40, for making a microcapillary with a pair of (110) silicon wafers 42 and 44. A fixture 46 has a vertical fitting post 48 formed on it that fits a pair of vertical alignment holes 50 and 52 in wafers 42 and 44. The fitting post 48 and alignment holes 50 and 52 are well-matched by anisotropic etching of silicon, e.g., with potassium hydroxide (KOH), or ethylenediamine pyrocatechol and water (EPW). A set of two pairs of matching semicircular microchannels 54, 56, 58 and 60 are isotropically etched into the wafers 42 and 44 on mating bonding surfaces. The wafers 42 and 44 are bonded together using the fixture 46 to cam the holes 50 and 52 into precise alignment with one another with the fitting post 48. The bonding may comprise eutectic, oxide, direct oxide growth, anodic or low-temperature glass bonding. A pair of microcapillaries 62 and 64 are thus formed.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A method for making circular tubular channels with two silicon wafers, comprising:

coating a first surface of a first silicon wafer with a first protective coating resistant to etching;

coating a second surface of a second silicon wafer with a second protective coating resistant to etching;

patterning a first slit entry in said first protective coating along a narrow path defined for a wider tubular channel in said first surface of said first silicon wafer;

patterning a second slit entry, which is a mirror-image of said first slit entry, in said second protective coating along said narrow path defined for said tubular channel in said second surface of said second silicon wafer;

isotropically etching said first and second surfaces of said first and second silicon wafers through said first and second slit entries such that said first and second silicon wafer are eroded equally in all directions from said slit entries, wherein respective halves of said tubular channel are formed, each having a semicircular cross section; and joining together said first and second silicon wafers at said first and second surfaces with said respective halves of said tubular channel aligned to produce an overall circular cross section for said tubular channel.

2. The method of claim 1, further comprising before the step of joining:

etching an alignment means into said first and second silicon wafers for precision matching of two parts of said tubular channel providing for after the step of joining a whole tubular channel that has a round cross section.

3. The method of claim 2, wherein:

the etching of said alignment means provides for a visual alignment window disposed in said first silicon wafer having a through hole and a corresponding visual alignment target disposed in said second silicon wafer having a depression, wherein said through hole and said depression, when coaxially aligned, visually signal a correct microscopic alignment of said first and second silicon wafers.

4. The method of claim 2, wherein:

the etching of said alignment means provides for a first vertical alignment hole in said first silicon wafer and a corresponding second vertical alignment hole in said second silicon wafer; and further providing a step for forming a pin disposed in said first and second vertical alignment holes for physically-forcing a microscopic alignment of said first and second silicon wafers.

5. The method of claim 2, wherein:

the etching of said alignment means provides for an alignment cavity in said first silicon wafer and a corresponding alignment post in said second silicon wafer for physically-forcing a microscopic alignment of said first and second silicon wafers.

6. The method of claim 2, wherein:

the etching of said alignment means provides for a first and a second vertical alignment hole in said first silicon wafer and a corresponding pair of third and fourth vertical alignment holes in said second silicon wafer, and a pair of loose-fitting pins each simultaneously disposed in said first and third vertical alignment holes and said second and fourth alignment holes provide for physically-forcing a microscopic alignment of said first and second silicon wafers when said pins are pulled apart from one another.

7. The method of claim 6, wherein:

the etching of said alignment means is such that said first through fourth vertical alignment holes are rectangular in plan view and have walls which narrow toward said bonding surfaces, and said pair of loose-fitting pins are each cylindrical in shape, wherein a two-point contact is made with each of said first through fourth vertical alignment holes.

* * * * *